(12) United States Patent
Kini et al.

(10) Patent No.: US 6,565,834 B2
(45) Date of Patent: May 20, 2003

(54) SKIN COMPOSITION

(75) Inventors: Mridula Kini, Mumbai (IN); Lalitagauri Rajwade, Mumbai (IN); Pushker Sona, Mumbai (IN); Ramesh Surianarayanan, Mumbai (IN)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/079,124

(22) Filed: Feb. 19, 2002

(65) Prior Publication Data
US 2002/0168329 A1 Nov. 14, 2002

(51) Int. Cl.⁷ .............. A61K 7/42; A61K 7/44; A61K 7/00
(52) U.S. Cl. ............ 424/59; 424/60; 424/400; 424/401
(58) Field of Search ............ 424/59, 60, 400, 424/401

(56) References Cited

U.S. PATENT DOCUMENTS 5,891,451 A    4/1999   Guerrero et al.

FOREIGN PATENT DOCUMENTS

| WO | 97/17060 | 5/1997 |
| WO | 97/30691 | 8/1997 |
| WO | 98/23257 | 6/1998 |

OTHER PUBLICATIONS

GB Search Report No. GB 0111173.1 dated Nov. 6, 2001, 1 page.

*Primary Examiner*—Shelley A. Dodson
(74) *Attorney, Agent, or Firm*—Ellen Plotkin

(57) ABSTRACT

Improved skin compositions which are capable of reducing oil and grease secretion from the skin comprising a combination of niacinamide and a $C_{11}$–$C_{30}$ alkyl or alkenyl ester of salicylic acid formulated in a specific carrier such as a vanishing cream base are disclosed.

7 Claims, No Drawings

SKIN COMPOSITION

The invention relates to a composition capable of reducing oil and grease secretion from skin. It is particularly found useful to have the formulation in a vanishing cream base.

Sebum is produced by the disruption of the cells in which it is formed (in the basal layer of the gland). This function may be termed holocrine secretion. Being liquid inside the duct and hair follicle, sebum diffuses up and down the follicular canal. Upon reaching the skin surface it combines with epithelial lipids (from the keratinizing cells) and emulsifies as an oily liquid with water from the sweat glands. In this way a semi-solid, slightly acidic, hydrophilic film is formed on the skin and in the hair follicles.

The quantity of sebum produced is directly proportional to the size of the gland. The rate of sebum production varies in different individuals, some having oilier skins than others. Male sex hormones increase sebum production. Increased temperature also increases production.

The literature is replete with methods and compositions for eliminating, treating or at least reducing the levels of skin oils and greasiness. None have proved totally satisfactory.

WO9823257 (Unilever) discloses a cosmetic method for reducing or inhibiting oil and grease generation from human skin by applying a C11–C30 alkyl or alkenyl ester of salicylic acid. WO9717060 (Procter and Gamble) discloses a topical composition comprising niacinamide and other actives for regulating the shiny or oily appearance of the skin.

The cosmetically acceptable carriers are one or more compatible solid or liquid fillers or diluents, and these are chosen based on the product type. Cosmetic compositions to deliver different benefit agents are prepared using different emulsifying systems and vehicles. Vanishing cream base, which generally comprises fatty acids and alkali metal soaps, is one of the preferred forms of such a cosmetically acceptable vehicle as this gives a desirable matt feel to the skin.

It is an advantage of the present invention to be able to provide an improved method for controlling, reducing or inhibiting oiliness and greasiness in human skin. It has been found that when a combination of niacinamide and $C_{11}$–$C_{30}$ alkyl or alkenyl ester of salicylic acid are formulated in a specific carrier such as a vanishing cream base there is a synergistic benefit on oil control of the skin.

According to a first aspect of the invention, there is provided a cosmetic composition for reducing or inhibiting oiliness and greasiness in human skin which involves topical application to the skin of a safe and effective amount of salicylate ester and niacinamide in a vanishing cream base as the carrier, wherein the salicylate ester has the formula $C_6H_4COOROH$ wherein R is a $C_{11}$–$C_{30}$ alkyl or alkenyl radical.

Thus according to an aspect the invention of the cosmetic composition comprises:

a. 5 to 25% by weight $C_{12}$–$C_{20}$ fatty acids;
b. 0.1 to 10% by weight surfactant;
c. 0.01 to 10% niacinamide;
d. 0.01 to 10% $C_{11}$–$C_{30}$ alkyl or alkenyl ester of salicylic acid;
e. optionally other skin lightening agent(s).

According to a preferred aspect of the invention the cosmetic composition comprises:

a. 5–25% by weight $C_{12}$–$C_{20}$ fatty acids;
b. 0.1–10% by weight fatty acid soap;
c. 0.01 to 10% niacinamide;
d. 0.01–10% tridecyl ($C_{13}$) salicylic acid;
e. optionally other skin lightening agent(s).

Now it has been found that oil and grease production by skin may be controlled, reduced and/or inhibited through application of a cosmetic composition including as active a derivative of salicylic acid having formula $C_6H_4COOROH$ wherein R is a $C_{11}$–$C_{30}$ alkyl or alkenyl radical in combination with niacinamide in a vanishing cream base. The composition essentially contains fatty acid as the main oil phase which is emulsified by surfactants. The surfactant may be anionic, nonionic, cationic or amphoteric and is preferably fatty acid soap.

By the term "skin" is meant to include all areas containing sebaceous glands, such as face, back, chest and scalp.

The salicylate esters will generally be amounts in the range from 0.01 to 10%, preferably from 0.1 to 5%, optimally from 0.1 to 3% by weight of the composition. Niacinamide will generally be in the range 0.01 to 10% and more preferably 0.1–3%. The two are preferably formulated in a vanishing cream base comprising 5–25% by weight $C_{12}$–$C_{20}$ fatty acids and 0.1–10% by weight of a surfactant, which is preferably fatty acid soap.

The surfactant may be selected from anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; block copolymers (ethylene oxide/ propylene oxide); and polyoxyethylene sorbitan, as well as combinations thereof. Alkyl polyglycosides and saccharide fatty amides (e.g. methyl gluconamides) are also suitable nonionic surfactants.

Preferred anionic surfactants are soap, and others such as alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Further examples of suitable surfactant compounds may be chosen from the commonly used actives described in "Surfactants in Cosmetics", II Edition, 1997, Eds. M. M. Rieger and L. D. Rhein, Marcel Dekker Inc. New York.

Emollient materials may also serve as pharmaceutically physiologically and/or cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethyl- siloxanes containing from 3 to 9, preferably from 4 to 5, silicon atoms. Linear volatile silicone materials generally have viscosities less than 5 centistokes at 25° C. while cyclic materials typically have viscosities of less than 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from 5 to 100,000 centistokes at 25° C. Among the preferred non-volatile emollients useful in the present compositions are the polydimethyl siloxanes having viscosities from 10 to 400 centistokes at 25° C.

Among the suitable ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples thereof.

Fatty acids having from 10 to 30 carbon atoms may also be included as pharmaceutically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as pharmaceutically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably polyethylene glycol. The amount of humectant may range anywhere from 0.5 to 30%, preferably between 1 and 15% by weight of the composition.

Thickeners may also be utilized as part of the pharmaceutically acceptable carrier of compositions according to the present invention. Typical thickeners include crosslinked acrylates (e.g. Carbopol 9820), hydrophobically-modified acrylates (e.g. Carbopol 1382), cellulosic derivatives and natural gums. Among useful cellulosic derivatives are sodium carboxymethyl cellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the pharmaceutically acceptable carrier in amounts from 1 to 99.9%, preferably from 80 to 99% by weight.

Cosmetic compositions of the present invention may be in any form. These forms may include emulsified systems such as lotions and creams, microemulsions, roll-on formulations, mousses, ointments (hydrophilic and hydrophobic), aerosol and non-aerosol sprays and pad-applied formulations.

Sunscreen actives may also be included in compositions of the present invention. Particularly preferred are such materials as ethylhexyl p-methoxycinnamate, available as Parsol MCX, and benzophenone-3, also known as Oxybenzone.

Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid.

Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain water-soluble vitamins. The term water-soluble defines substances with a solubility of at least 0.1%, preferably at least 1%, optimally at least 5% by weight in water.

Illustrative water-soluble vitamins are Niacin, Vitamin $B_6$, Vitamin C and Biotin. One source for Vitamin C is a product sold under the trademark of Vitazyme C available from the Brooks Company. Niacin, Vitamin B and Biotin are available from Roche Pharmaceuticals. Total amount of vitamins in compositions according to the present invention may range from 0.001 to 1%, preferably from 0.01 to 0.6, optimally from 0.1 to 0.5% by weight.

Keratolytic agents such as $C_2$–$C_{25}$ α-hydroxy alkanoic acids may also be incorporated into compositions of this invention. Illustrative of this group of materials are glycolic, lactic, α-hydroxyoctanoic acids and salts thereof. The salts may be selected from alkalimetal, ammonium and $C_1$–$C_2$, alkyl or alkanclammonium counterions. Levels of α-hydroxyalkanoic acids may range from 0.001 to 8%, preferably between 0.2 and 1%, optimally between 0.4 and 0.5% by weight.

Minor adjunct ingredients may also be present in the cosmetic compositions. Among them may be the water-insoluble vitamins such as vitamin A palmitate, vitamin E acetate and DL-panthenol. Another adjunct ingredient can be that of an enzyme. Particularly preferred is superoxide dismutase, commercially available as Biocell SOD from Brooks Industries, USA. Natural vegetable materials from renewable resources are often desirable in cosmetic compositions. For instance, cosmetic compositions of the present invention may include P-glucan derived from oats, commercially available under the trademark Microat SF from Nurture Inc., Missoula, Mt.

Colorants, fragrances, opacifiers, adsorbents and abrasives may also be included in compositions of the present invention. Each of these substances may range from 0.05 to 5%, preferably between 0.1 and 3% by weight.

The following Examples will more fully illustrate embodiments of this invention.

All parts, percentages and proportions referred to herein and in the appended claims are by weight of the composition unless otherwise indicated.

EXAMPLES

Example 1

Comparison of the Effect on Reduction in Oil or Grease Secretion

The formulations as indicated in Table 1 were prepared by dissolving the oil soluble and water soluble components separately and homogenisng the two in a conventional manner. Example 1 was the control formulation where no active ingredients such as niacinamide or tridecyl salicylate were added. In Example 2 niacinamide, Example 3 tridecyl salicylate and in Example 4 both niacinamide and tridecyl salicylate were added.

Method of Testing Oil Secretion

The above mentioned formulations (Examples 1 to 4) were tested for their efficacy in reducing the oil secretion on the skin using a sebumeter by the following protocol.

Volunteers with oily skin type were recruited. The initial sebum was measured with Sebumeter SM 810 PC on the cheeks, and the selection was made such that they had approximately similar sebum profile. The panellists were asked to use 0.5 g of the assigned cream on their face twice a day, for one week. The sebum profile was measured on the $8^{th}$ day. The panellists washed their face and the sebum secretion on the skin surface after 2 hours was measured using the Sebumeter SM 810 PC on the cheeks.

Sebumeter is a device for measuring sebum content on skin surface. A piece of plastic film (wound in the form of a cassette) is kept on the skin for 30 sec. By this means the 64 mm measuring area of the plastic film becomes transparent due to absorbed sebum. This results in a change of the light filtering through & therefore the amount of sebum can be measured & evaluated photometrically as soon as the cassette is inserted in the sebumeter. Sebumeter SM 810 PC immediately indicates sebum content between 50 & 300 $\mu gm/cm^2$ % sebum reduction is calculated.

TABLE 1

| Composition (% wt.) | Example 1 | Example 2 | Example 3 | Example 4 |
|---|---|---|---|---|
| Stearic acid | 15.3 | 15.3 | 15.3 | 15.3 |
| Cetyl alcohol | 0.20 | 0.20 | 0.20 | 0.20 |
| Dimethicone | 0.50 | 0.50 | 0.50 | 0.50 |
| Tridecyl salicylate | — | — | 0.25 | 0.25 |
| Polyethylene glycol | 3.00 | 3.00 | 3.00 | 3.00 |
| Potassium hydroxide 85% | 0.405 | 0.405 | 0.405 | 0.405 |
| Niacinamide | — | 0.50 | — | 0.50 |
| Methyl paraben | 0.20 | 0.20 | 0.20 | 0.20 |
| Acrylic acid copolymer | 0.10 | 0.10 | 0.10 | 0.10 |
| Precipitated Silica | 0.40 | 0.40 | 0.40 | 0.40 |
| Phenoxyethanol | 0.20 | 0.20 | 0.20 | 0.20 |
| Perfume | 0.50 | 0.50 | 0.50 | 0.50 |

TABLE 1-continued

| Composition (% wt.) | Example 1 | Example 2 | Example 3 | Example 4 |
|---|---|---|---|---|
| Water | To 100 | To 100 | To 100 | To 100 |
| % Reduction in sebum secretion after 2 hours | −9.28 | −17.14 | −10.94 | −42.03 |

The data presented in Table 1 show that after 2 hours niacinamide and tridecyl salicylate have significant effect in reducing oil secretion on the skin. However, the combination of niacinamide and tridecyl salicylate is superior to either niacinamide or tridecyl salicylate alone.

Comparison of the Efficacy of Vanishing Cream Base

The actives niacinamide and tridecyl salicylate were formulated in a vanishing cream base and also in a cosmetic base containing no adsorbents (Example 5) or with it (Example 6). The formulation of the actives in vanishing cream base is as in Example 4. The formulation of a cosmetic base with the actives is given in Table 2.

TABLE 2

| Composition (% wt.) | Example 5 | Example 6 |
|---|---|---|
| Magnesium silicate | — | 5.00 |
| Stearated calcium carbonate | — | 5.00 |
| Propylene glycol | 2.50 | 2.50 |
| Precipitated Silica | — | 1.50 |
| Cetostearyl alcohol | 3.00 | 3.00 |
| Polyacrylamide & C13–14 isoparaffin & Laureth-7 | 1.25 | 1.25 |
| Niacinamide | 0.5 | 0.5 |
| Tridecyl salicylate | 0.25 | 0.25 |
| POE-21 Stearyl ether | 0.75 | 0.75 |
| Xanthan gum | 0.60 | 0.60 |
| Perfume | 0.50 | 0.50 |
| Fumed silica | — | 0.50 |
| POE-2 Stearyl ether | 0.50 | 0.50 |
| Methyl paraben | 0.20 | 0.20 |
| Propyl paraben | 0.10 | 0.10 |
| Disodium EDTA | 0.05 | 0.05 |
| DM Water | To 100 | To 100 |

Comparison on % Reduction in Sebum Secretion

The protocol to measure the % reduction in sebum secretion is as per the procedure described above. The samples of creams described in Examples 4, 5 and 6 were tested for their efficacy in reducing the sebum secretion and the data are presented in Table 3.

TABLE 3

| % Reduction in sebum secretion | Example 4 | Example 5 | Example 6 |
|---|---|---|---|
| After 2 hours | −55.3 | −27.0 | 7.7 |

The data show that the efficacy of the actives when present in a vanishing cream base is far superior to that in any other cosmetic cream base. Even when additional adsorbents are added to mop up the sebum the vanishing cream base proved superior.

What is claimed is:

1. A cosmetic composition for reducing or inhibiting oiliness and greasiness comprising:
   (a) 5–25% by wt. of a $C_{12}$–$C_{20}$ fatty acid;

(b) 0.1%–10% of one or more surfactants selected from the group consisting of anionic, nonionic, cationic and amphoteric surfactants;

(c) 0.01–10% of niacinamide;

(d) 0.01%–10% of a $C_{11}$–$C_{30}$ alkyl or alkenyl ester of salicylic acid; and (e) a cosmetically acceptable carrier, wherein the cosmetically acceptable carrier is an emollient material selected from the group consisting of silicone oils, synthetic esters and mixtures thereof.

2. A composition as claimed in claim 1 wherein the surfactant is an anionic surfactant selected from fatty acid soap, alkyl ether sulfates or sulfonates, alkyl sulfates or sulfonates, alkylbenzene sulfonates, alkyl and dialkyl sulfosuccinates, $C_8$–$C_{20}$ acyl isethionates, acyl glumates, $C_8$–$C_{20}$ alkyl ether phosphates or combinations thereof.

3. A composition as claimed in claim 2 wherein the anionic surfactant is a fatty acid soap.

4. A composition as claimed in claim 1 wherein the $C_{11}$–$C_{30}$ alkyl or alkenyl ester of salicylic acid is tridecyl salicylate.

5. A composition as claimed in claim 1 further comprising an additional skin-lightening agent.

6. A composition as claimed in claim 1 further comprising 0.1%–30% of a sunscreen active.

7. A cosmetic method of controlling, reducing and/or inhibiting the production of oil and grease in human skin comprising applying a composition according to claim 1 to the skin.

* * * * *